US009939658B1

(12) United States Patent
Gutierrez et al.

(10) Patent No.: US 9,939,658 B1
(45) Date of Patent: Apr. 10, 2018

(54) AUTONOMOUS EYE TRACKING CONTACT LENS (71) Applicant: Verily Life Sciences LLC, Mountain View, CA (US)

(72) Inventors: Christian Gutierrez, San Jose, CA (US); Shungneng Lee, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 15/144,358

(22) Filed: May 2, 2016

(51) Int. Cl.
A61B 3/14 (2006.01)
G02C 7/08 (2006.01)
A61B 3/113 (2006.01)
G02C 7/04 (2006.01)

(52) U.S. Cl.
CPC .............. G02C 7/083 (2013.01); A61B 3/113 (2013.01); G02C 7/04 (2013.01)

(58) Field of Classification Search
USPC .................................................. 351/200–246
See application file for complete search history.

(56) References Cited

U.S. PATENT DOCUMENTS

| 9,144,376 B2 | 9/2015 | Guth et al. |
| 2006/0146281 A1 | 7/2006 | Goodall et al. |
| 2007/0010757 A1 | 1/2007 | Goodall et al. |
| 2012/0245444 A1 | 9/2012 | Otis et al. |
| 2014/0268035 A1 | 9/2014 | Pugh et al. |
| 2014/0327875 A1 | 11/2014 | Blum et al. |
| 2015/0362754 A1* | 12/2015 | Etzkorn .................. G02C 7/083 351/159.03 |
| 2015/0362756 A1* | 12/2015 | Wiser ..................... G02C 7/083 351/210 |
| 2016/0058315 A1* | 3/2016 | Wiser .................. A61B 5/6821 600/340 |

(Continued)

FOREIGN PATENT DOCUMENTS

WO WO 2014/194432 A1 12/2014

OTHER PUBLICATIONS

LC Technologies, Inc., "Superior Eye Tracking Technology," www.eyegaze.com, 2012, 8 pages.

(Continued)

Primary Examiner — Mohammed Hasan
(74) Attorney, Agent, or Firm — Christensen O'Connor Johnson Kindness PLLC (57) ABSTRACT An eye-mountable device including a lens operable to be removably mounted on a corneal surface of an eye and to be compatible with a motion of an eyelid; a photosensor coupled to the lens, the photosensor including a light detecting surface oriented to detect light from an iris of the eye; and an accommodation actuator coupled to the lens and operable to modify an optical power of the lens in response to light detected by the photosensor. A method including monitoring a signal from a photosensor coupled to a contact lens, the signal representative of light reflected from an iris of an eye on which the contact lens is mounted; detecting a change in a gazing direction of the eye based on the signal; and modifying an optical power of the contact lens in response to the detect change in gazing direction.

19 Claims, 4 Drawing Sheets (56) References Cited

U.S. PATENT DOCUMENTS

2016/0113760 A1* 4/2016 Conrad ............... A61F 2/1648
                                                      623/6.22
2017/0255026 A1* 9/2017 Rakhyani ............... A61B 3/113

OTHER PUBLICATIONS

SensoMotoric Instruments, "SMI Eye Tracking Glasses 2 Wireless: Mobile Eye Tracking Made Easy, Robust, Efficient and Versatile," www.eyetracking-glasses.com, 2015, 4 pages.

TobiiPro, "The World's Most Natural Wearable Eye Tracking System for Real-World Research," www.tobiipro.com, 4 pages.

\* cited by examiner

AUTONOMOUS EYE TRACKING CONTACT LENS

TECHNICAL FIELD

This disclosure relates generally to the field of optics, and in particular but not exclusively, relates to contact lenses.

BACKGROUND INFORMATION

Accommodation is a process by which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and applies a force on the elastic lens during muscle contractions that change the focal point of the elastic lens.

As an individual ages, the effectiveness of the ciliary muscle degrades. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide today (110 million in the United States alone) and that number is expected to substantially rise as the world's population ages. Techniques and devices that can help individuals offset the effects of Presbyopia are increasingly in demand.

BRIEF DESCRIPTION OF THE DRAWINGS

Non-limiting and non-exhaustive embodiments are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus, system and methods of operation for an eye-mountable device such as a contact lens with capacitive gaze tracking and accommodation are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Described herein is a smart contact lens or eye-mountable device that includes gaze detection circuitry and logic for identifying the direction or focal distance of a gaze of a wearer of the device and using this information for real-time feedback control of an accommodation actuator. Embodiments of an eye-mountable device may include power supply circuitry, control electronics, an accommodation actuator, one or more photosensors, and an optional antenna all embedded within an enclosure material formed to be contact mounted to an eye. The photosensor includes a light-detecting surface oriented to detect light reflected from an iris of an eye on which the device is mounted or worn. The control electronics are coupled to monitor the one or more photosensors to identify gaze direction/focal distance, manipulate the accommodation actuator to control the optical power of the eye-mountable device, and optionally provide wireless communications with an external reader. In some embodiments, the power supply may include charging circuitry for controlling inductive wireless charging of an embedded battery.

The enclosure material may be fabricated of a variety of materials compatible for direct contact with a human eye and in the form of a round lens with a concave curvature configured to mount to a corneal surface of an eye. The electronics can be disposed upon a substrate embedded within the enclosure material representatively near its periphery or in an outer radius to avoid interference with incident light received closer to the central region of the cornea. In one embodiment, the substrate is transparent or a portion or portions of the substrate on which one or more photosensors are connected thereto is transparent so that a light detecting surface of the one or more photosensors is mounted face down on the substrate to detect backscatter light from an iris through the substrate and enclosure material.

In some embodiments, the gaze direction/focal distance information provided by the control electronics through monitoring the photosensor(s) can be used to determine an amount of accommodation to be applied via a see-through accommodation actuator positioned in a central portion or inner radius of the enclosure material. The accommodation actuator is connected to the controller to be electrically manipulated thereby. For example, the accommodation actuator may be implemented with a liquid crystal cell that changes its index of refraction in response to an applied electrical bias signal. In other embodiments, the accommodation actuator may be implemented using other types of electro-active optical materials such as electro-optic materials that vary refractive index in the presence of an applied electric field or electro-mechanical structures that change the shape of a deformable lens. Other example structures that may be used to implement the accommodation actuator include electro-wetting optics, micro-electro-mechanical systems, or otherwise.

Figure 1:
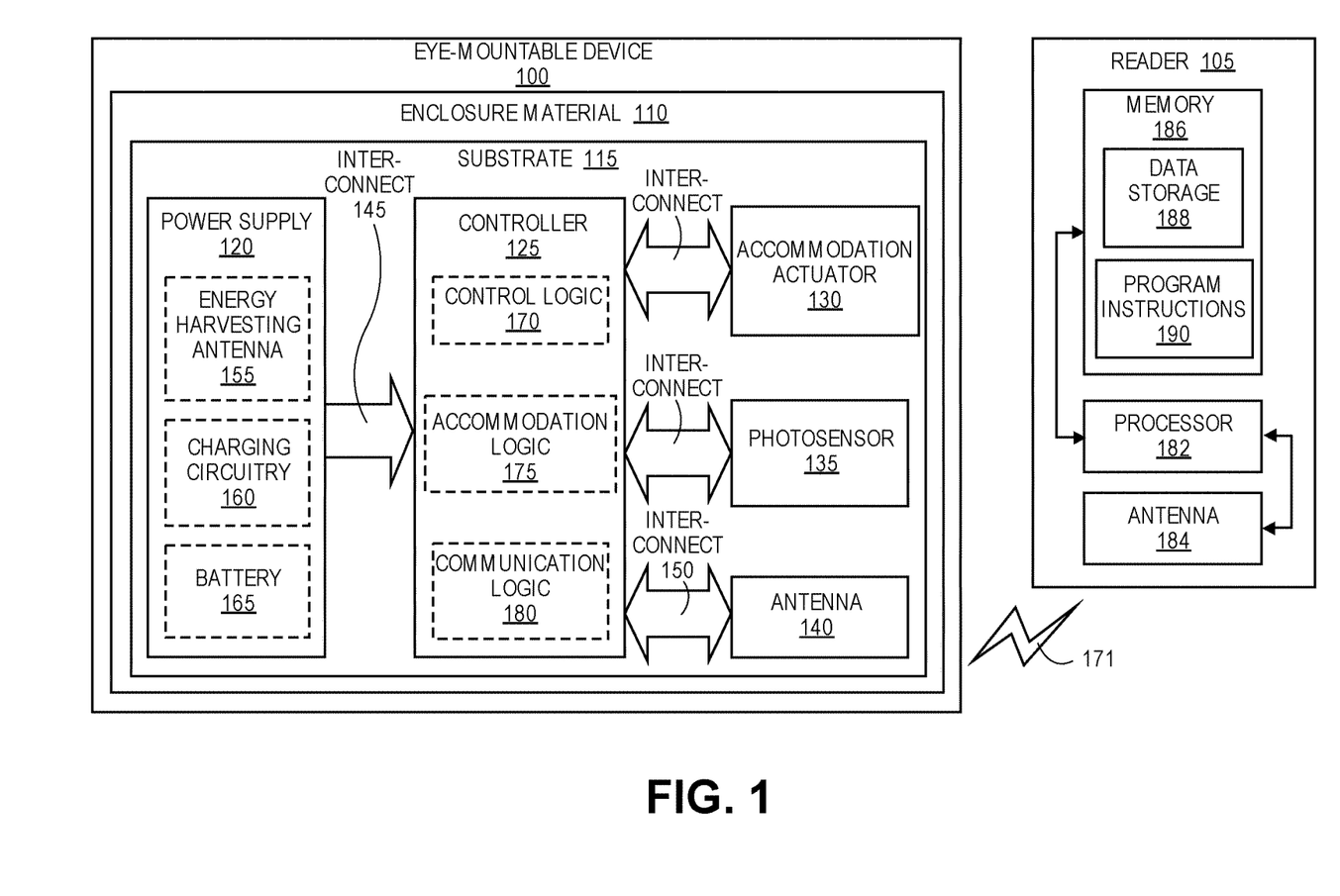
FIG. 1 is a functional block diagram of an eye-mountable device including a photosensor system of one or more photosensors with a light-detecting surface oriented to detect reflected or back-scattered light from an iris of a wearer of the device.

FIG. 1 is a functional block diagram of an eye-mountable device with photosensor tracking for auto-accommodation along with an external reader, in accordance with an embodiment of the disclosure. The exposed portion of eye-mountable device 100 includes enclosure material 110 formed to be contact-mounted to a corneal surface of an eye. Substrate 115 is embedded within or surrounded by enclosure material 110 to provide a mounting surface for power supply 120, controller 125, accommodation actuator 130, photosensor system 135, antenna 140, and various interconnects 145 and 150. The illustrated embodiment of power supply 120 includes energy harvesting antenna 155, charging circuitry 160, and battery 165. The illustrated embodiment of controller 125 includes control logic 170, accommodation logic 175, and communication logic 180. The illustrated embodiment of reader 105 includes a processor 182, antenna 184, and memory 186. The illustrated embodiment of memory 186 includes data storage 188 and program instructions 190.

Controller 125 is connected to receive signals (e.g., current signals) from photosensor system 135 and further connected to operate accommodation actuator 130. Power supply 120 supplies operating voltages to controller 125 and/or the accommodation actuator 130. Antenna 140 is operated by controller 125 to communicate information to and/or from eye-mountable device 100. In one embodiment, antenna 140, controller 125, power supply 120, and photosensor system 135 are all situated on embedded substrate 115. In one embodiment, accommodation actuator 130 is embedded within enclosure material 110, but is not disposed on substrate 115. Because eye-mountable device 100 includes electronics and is configured to be contact-mounted to an eye, it is also referred to herein as an ophthalmic electronics platform, contact lens, or smart contact lens.

To facilitate contact-mounting, the enclosure material 110 can have a concave surface configured to adhere ("mount") to a moistened corneal surface (e.g., by capillary forces with a tear film coating the corneal surface). Additionally or alternatively, eye-mountable device 100 can be adhered by a vacuum force between the corneal surface and enclosure material 110 due to the concave curvature. While mounted with the concave surface against the eye, the outward-facing surface of enclosure material 110 can have a convex curvature that is formed to not interfere with eye-lid motion while eye-mountable device 100 is mounted to the eye. For example, enclosure material 110 can be a substantially transparent curved disk shaped similarly to a contact lens.

Enclosure material 110 can include one or more biocompatible materials, such as those employed for use in contact lenses or other ophthalmic applications involving direct contact with the corneal surface. Enclosure material 110 can optionally be formed in part from such biocompatible materials or can include an outer coating with such biocompatible materials. Enclosure material 110 can include materials configured to moisturize the corneal surface, such as hydrogels and the like. In some instances, enclosure material 110 can be a deformable ("non-rigid") material to enhance wearer comfort. In some instances, enclosure material 110 can be shaped to provide a predetermined, vision-correcting optical power, such as can be provided by a contact lens. Enclosure material may be fabricated of various materials including a polymeric material, a hydrogel, polymethyl methacrylate (PMMA), silicone based polymers (e.g., fluoro-silicon acrylate), or otherwise.

Substrate 115 includes one or more surfaces suitable for mounting the photosensor system 135, controller 125, power supply 120, and antenna 140. Substrate 115 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on substrate 115 to form circuitry, electrodes, etc. For example, antenna 140 can be formed by depositing a pattern of gold or another conductive material on substrate 115. Similarly, interconnects 145 and 150 can be formed by depositing suitable patterns of conductive materials on substrate 115. A combination of resists, masks, and deposition techniques can be employed to pattern materials on substrate 115. In one embodiment, substrate 115 is a transparent material such as a polyimide, polyethylene terephthalate ("PET") or a poly (p-xylylene) polymer (a Parylene). Substrate 115 can be a relatively rigid material, such as PET or another material sufficient to structurally support the circuitry and/or electronics within enclosure material 110. Eye-mountable device 100 can alternatively be arranged with a group of unconnected substrate portions rather than a single substrate. For example, controller 125 and power supply 120 can be mounted to one substrate portion, while antenna 140 and photosensor system 135 are mounted to another substrate portion or to individual substrate portions and the substrate portions can be electrically connected via interconnects. As noted above, it is desired, in one embodiment, for the one or more photosensors of photosensor system 135 to be connected to a substrate of a transparent or light transmissive (with minimal scattering) material so that a photosensor connected to the substrate can detect backscatter light from an iris through the substrate. Where substrate portions are utilized rather than a unitary substrate body, a portion to which a photosensor is connected may be transparent or light transmissive while a portion to which controller 125 or power supply 120 are connected need not be or may be less transparent or less light transmissive.

In some embodiments, power supply 120 and controller 125 (and the substrate 115) can be positioned away from the center of eye-mountable device 100 and thereby avoid interference with light transmission to the eye through the center of eye-mountable device 100. In contrast, accommodation actuator 130 can be centrally positioned to apply optical accommodation to the light transmitted to the eye through the center of eye-mountable device 100. For example, where eye-mountable device 100 is shaped as a concave-curved disk, substrate 115 can be embedded around the periphery (e.g., near the outer circumference) of the disk. Representatively, eye-mountable device 100 may be defined by an inner radius portion and an outer radius portion. Substrate 115 is embedded in the outer radius portion and power supply 120 and controller 125, in one embodiment, are connected to substrate 115 of eye-mountable device 110 such that each is positioned within the outer radius of eye-mountable device 100 while accommodation actuator is connected to the device such that it is positioned in the inner radius portion. In some embodiments, photosensor system 135 includes one or more discrete photosensors such as photodiodes that are peripherally distributed in the outer radius portion. The one or more photosensors of photosensor system 135 are connected to eye-mountable device 100 such that the photosensing portion of the one or more photosensors detect light reflected from an iris of an eye on which the device is worn. The reflected light or backscattered light refers to light received into the eye from a light source (direct light) that is reflected by an iris portion of the eye.

Substrate 115 can be shaped as a flattened ring with a radial width dimension sufficient to provide a mounting platform for the embedded electronics components. Substrate 115 can have a thickness sufficiently small to allow the substrate to be embedded in enclosure material 110 without adversely influencing the profile of eye-mountable device 100. Substrate 115 can have a thickness sufficiently large to provide structural stability suitable for supporting the electronics mounted thereon. For example, substrate 115 can be shaped as a ring with a diameter of about 10 millimeters, a radial width of about 1 millimeter (e.g., an outer radius 1 millimeter larger than an inner radius), and a thickness of about 50 micrometers. Substrate 115 can optionally be aligned with the curvature of the eye-mounting surface of eye-mountable device 100 (e.g., convex surface). For example, substrate 115 can be shaped along the surface of an imaginary cone between two circular segments that define an inner radius and an outer radius. In such an example, the surface of substrate 115 along the surface of the imaginary cone defines an inclined surface that is approximately aligned with the curvature of the eye-mounting surface at that radius.

In the illustrated embodiment, power supply 120 includes battery 165 to power the various embedded electronics, including controller 125. Battery 165 may be inductively charged by charging circuitry 160 and energy harvesting antenna 155. In one embodiment, antenna 140 and energy harvesting antenna 155 are independent antennae, which serve their respective functions of energy harvesting and communications. In another embodiment, energy harvesting antenna 155 and antenna 140 are the same physical antenna that are time shared for their respective functions of inductive charging and wireless communications with reader 105. Additionally or alternatively, power supply 120 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 160 may include a rectifier/regulator to condition the captured energy for charging battery 165 or directly power controller 125 without battery 165. Charging circuitry 160 may also include one or more energy storage devices to mitigate high frequency variations in energy harvesting antenna 155. For example, one or more energy storage devices (e.g., a capacitor, an inductor, etc.) can be connected to function as a low-pass filter.

Controller 125 contains logic to choreograph the operation of the other embedded components. Control logic 170 controls the general operation of eye-mountable device 100, including providing a logical user interface, power control functionality, etc. Accommodation logic 175 includes logic for monitoring signals from photosensor system 135 (e.g., current signals), determining the current gaze direction or focal distance of the user, and manipulating accommodation actuator 130 in response to a signal from photosensor system 135 to provide the appropriate accommodation. The auto-accommodation can be implemented in real-time based upon signals from photosensor system 135, or permit user control to select specific accommodation regimes (e.g., near-field accommodation for reading, far-field accommodation for regular activities, etc.). Additional logic for detecting blinking of an eye of a wearer of the device, blink patterns or multiple sequential eye positions may also be included. Communication logic 180 provides communication protocols for wireless communication with reader 105 via antenna 140. In one embodiment, communication logic 180 provides backscatter communication via antenna 140 when in the presence of electromagnetic field 171 output from reader 105. In one embodiment, communication logic 180 operates as a smart wireless radio-frequency identification ("RFID") tag that modulates the impedance of antenna 140 for backscatter wireless communications. The various logic modules of controller 125 may be implemented in software/firmware executed on a general purpose microprocessor, in hardware (e.g., application specific integrated circuit), or a combination of both.

Eye-mountable device 100 may include various other embedded electronics and logic modules. For example, a light source or pixel array may be included to provide visible feedback to the user. An accelerometer or gyroscope may be included to provide positional, rotational, directional or acceleration feedback information to controller 125.

It is noted that the block diagram shown in FIG. 1 is described in connection with functional modules for convenience in description, but does not necessarily connote physical organization. Rather, embodiments of eye-mountable device 100 can be arranged with one or more of the functional modules ("sub-systems") implemented in a single chip, multiple chips, in one or more integrated circuits, or otherwise.

External reader 105 includes antenna 184 (or group of more than one antennae) to send and receive wireless signals 171 to and from eye-mountable device 100. External reader 105 also includes a computing system with processor 182 in communication with memory 186. Memory 186 is a non-transitory computer-readable medium that can include, without limitation, magnetic disks, optical disks, organic memory, and/or any other volatile (e.g. RAM) or non-volatile (e.g. ROM) storage system readable by processor 182. Memory 186 can include data storage 188 to store indications of data, such as data logs (e.g., user logs), program settings (e.g., to adjust behavior of eye-mountable device 100 and/or external reader 105), etc. Memory 186 can also include program instructions 190 for execution by processor 182 to cause external reader 105 to perform processes specified by instructions 190. For example, program instructions 190 can cause external reader 105 to provide a user interface that allows for retrieving information communicated from eye-mountable device 100 or allows transmitting information to eye-mountable device 100 to program or otherwise select operational modes of eye-mountable device 100. External reader 105 can also include one or more hardware components for operating antenna 184 to send and receive wireless signals 171 to and from eye-mountable device 100.

External reader 105 can be a smart phone, digital assistant, or other portable computing device with wireless connectivity sufficient to provide wireless communication link 171. External reader 105 can also be implemented as an antenna module that can be plugged in to a portable computing device, such as in an example where communication link 171 operates at carrier frequencies not commonly employed in portable computing devices. In some instances, external reader 105 is a special-purpose device configured to be worn relatively near an eye of a wearer to allow wireless communication link 171 to operate with a low power budget. For example, external reader 105 can be integrated in a piece of jewelry such as a necklace, earring, etc. or integrated in an article of clothing worn near the head, such as a hat, headband, etc.

Figure 2A:
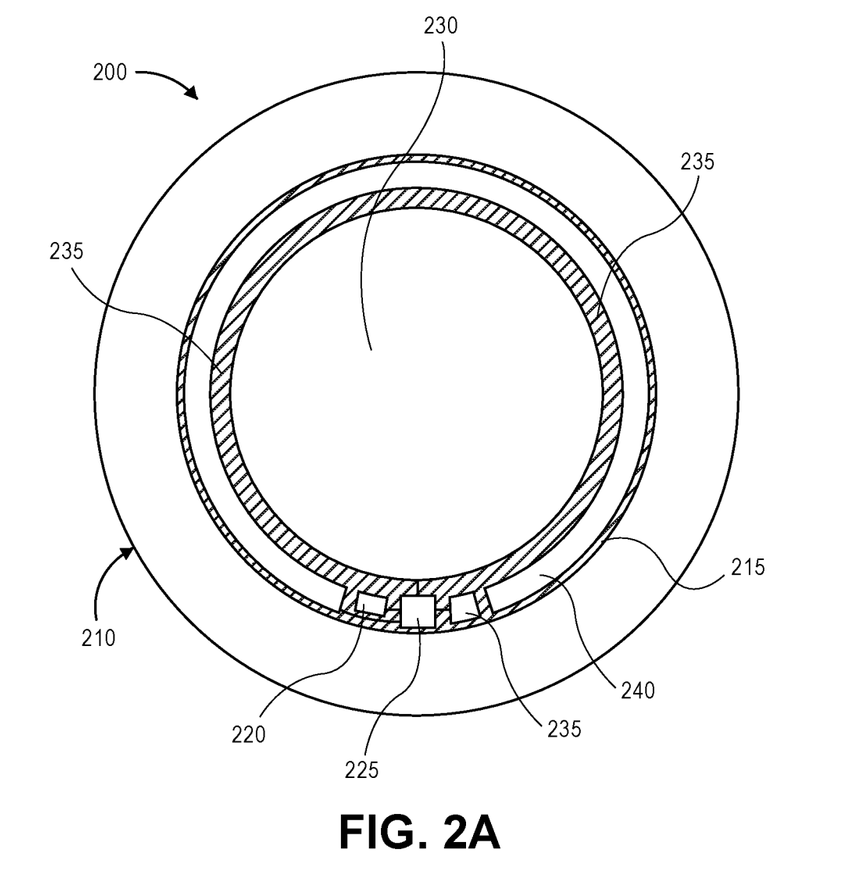
FIG. 2A is a top view of an eye-mountable device, in accordance with an embodiment of the disclosure.
Figure 2B:
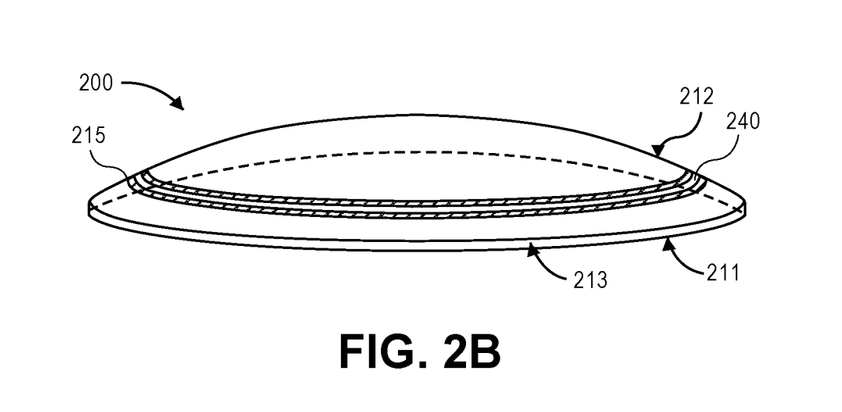
FIG. 2B is a perspective view of an eye-mountable device, in accordance with an embodiment of the disclosure.

FIGS. 2A and 2B illustrate two views of an eye-mountable device, in accordance with an embodiment of the disclosure. FIG. 2A is a top view of eye-mountable device 200 while FIG. 2B is a perspective view of the same.

Eye-mountable device 200 is one possible implementation of eye-mountable device 100 illustrated in FIG. 1. The illustrated embodiment of eye-mountable device 200 includes enclosure material 210, substrate 215, power supply 220, controller 225, accommodation actuator 230, photosensor system 235, and antenna 240. It should be appreciated that FIGS. 2A and 2B are not necessarily drawn to scale, but have been illustrated for purposes of explanation only in describing the arrangement of example eye-mountable device 200.

Enclosure material 210 of eye-mountable device 200 is shaped as a curved disk. Enclosure material 210 is a substantially transparent material to allow incident light to be transmitted to the eye while eye-mountable device 200 is mounted to the eye. Enclosure material 210 is a biocompatible material similar to those employed to form vision correction and/or cosmetic contact lenses in optometry, such as a polymeric material, polyethylene terephthalate ("PET"), polymethyl methacrylate ("PMMA"), polyhydroxyethylmethacrylate ("polyHEMA"), a hydrogel, silicon based polymers (e.g., fluoro-silicon acrylate) combinations of these, or otherwise. Enclosure material 210 can be formed with one side having concave surface 211 suitable to fit over a corneal surface of an eye. The opposite side of the disk can have convex surface 212 that does not interfere with eyelid motion while eye-mountable device 200 is mounted to the eye. In the illustrated embodiment, circular or oval outer side edge 213 connects concave surface 211 and convex surface 212.

Eye-mountable device 200 can have dimensions similar to a vision correction and/or cosmetic contact lenses, such as a diameter of approximately 1 centimeter, and a thickness of about 0.1 to about 0.5 millimeters. The diameter and thickness values are provided for explanatory purposes only. In some embodiments, the dimensions of eye-mountable device 200 can be selected according to the size and/or shape of the corneal surface of the eye of an intended wearer. Enclosure material 210 can be formed with a curved shape in a variety of ways. For example, techniques similar to those employed to form vision-correction contact lenses, such as heat molding, injection molding, spin casting, etc. can be employed to form enclosure material 210.

Substrate 215 is embedded within enclosure material 210. Substrate 215 can be embedded to be situated along the outer periphery or in an outer radius of enclosure material 210, away from the central region or inner radius where accommodation actuator 230 is positioned. In the illustrated embodiment, substrate 215 encircles accommodation actuator 230. Substrate 215 does not interfere with vision because it is too close to the eye to be in focus and is positioned in an outer radius portion of enclosure material 210 away from the central region where incident light is transmitted to the light-sensing portions of the eye. As noted above, in some embodiments, substrate 215 can be formed of a transparent material to further mitigate effects on visual perception and to permit transmission of backscatter light to be detected by one or more photosensors of a photosensor system connected to substrate 215. In another embodiment, substrate 215 may have an opening therethrough to accommodate a light-detecting surface of a photosensor. In such embodiment, substrate 215 may not be transparent. Substrate 215 can be shaped as a flat, circular ring (e.g., a disk with a centered hole). The flat surface of substrate 215 (e.g., along the radial width) is a platform for mounting electronics and for patterning conductive materials to form electrodes, antenna(e), and/or interconnections.

Photosensor system 235 including one or more photosensors, such as one or more photodiodes of a size to fit on substrate 215 and be present in a cornea of a wearer of eye-mountable device 200 without interference to the wearer. The one or more photosensors such as photodiodes are connected to substrate 215, representatively through flip-chip bonding, at a position so that a light-detecting surface of the one or more photosensors can detect light from an iris of a wearer of the eye-mountable device. In one embodiment, the one or more photosensors of photosensor system 235 is(are) situated or positioned along an outer periphery or outer radius of enclosure material 210. In one embodiment, when eye-mountable device 200 is mounted on a corneal surface of an eye of a wearer, at least a portion of the outer radius of enclosure material 210 is on an iris of the eye. The one or more photosensors of photosensor system 235 are, in one embodiment, correspondingly on at least a portion of the iris of the eye. In one embodiment, a light-detecting surface of each of the one or more photosensors is facing the iris in order to detect backscatter or light reflected from the iris. As noted above, where the light detecting surface of a photosensor faces substrate 215, the substrate and any bonding material are transparent to allow light transmission therethrough or the substrate has an opening through which backscatter light can pass to be detected by the light-detecting surface of a photosensor. The one or more photosensors, in one embodiment, are operable to convert detected light into a signal such as a current signal. By monitoring the amount of reflected light from the iris, signals from photosensor system 235 can be evaluated by controller 225 to determine the approximate gaze direction and/or focal distance.

In one embodiment, the one or more photosensors of photosensor system 235 may be positioned on any portion of an iris of a wearer. In this manner, the backscatter light measurement is not sensitive to a rotational orientation of eye-mountable device 200.

Figure 3A:
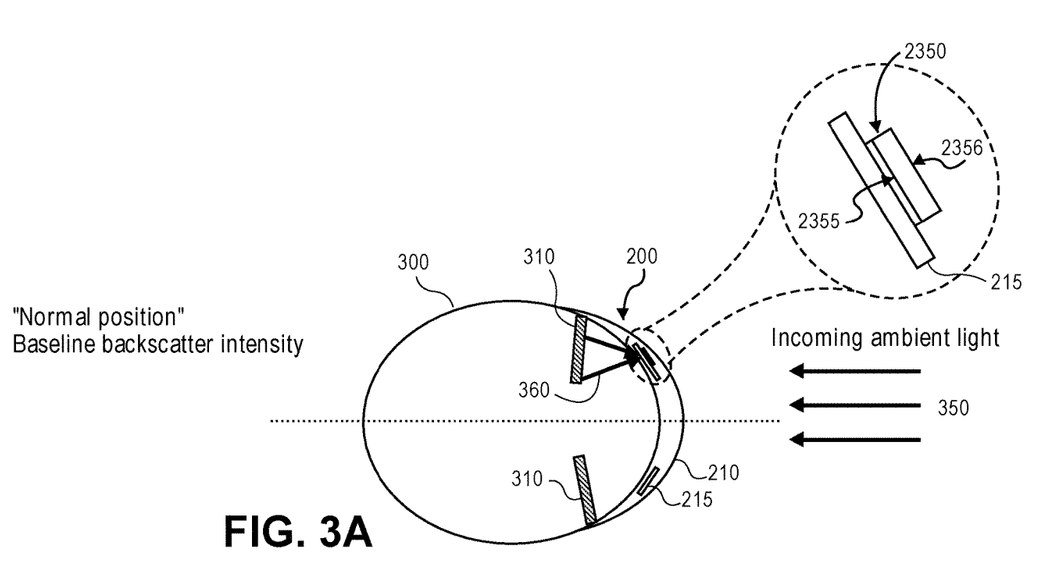
FIGS. 3A and 3B illustrate the general operation of a photosensor detection mechanism, in accordance with an embodiment of the disclosure.

Referring to FIG. 3A, eye-mountable device 200 is disposed on a cornea that is looking straight forward (e.g., looking in a line parallel to a line projecting from a top of the nose). FIG. 3A shows eye-mountable device 200 on the cornea including enclosure material 210 and substrate 215 (e.g., a ring) situated in an outer radius of the enclosure material. In this embodiment, substrate 215 is on or directly in front of iris 310 of eye 300. Connected to substrate 215 is photosensor 2350 that is, for example, a photodiode. Photosensor 2350 includes light detecting surface 2355 positioned in the direction of iris 310 with backside 2356 positioned toward ambient light source 350 (opposite light detecting surface 2355). FIG. 3A shows ambient light 350 producing backscatter light 360 of light reflected from iris 310. Backscatter light 360 is detected by photosensor 2350 and, in one embodiment, converted into a current signal. In one embodiment, the backscatter light signal when the cornea is looking straight ahead is a baseline signal. Controller 225 can determine that the cornea is looking straight forward via the signal from photosensor 2350. In this baseline signal scenario, controller 224 may determine that the user is focusing on the far-field and an accommodation of eye-mountable device 200 may be adjusted accordingly.

Figure 3B:
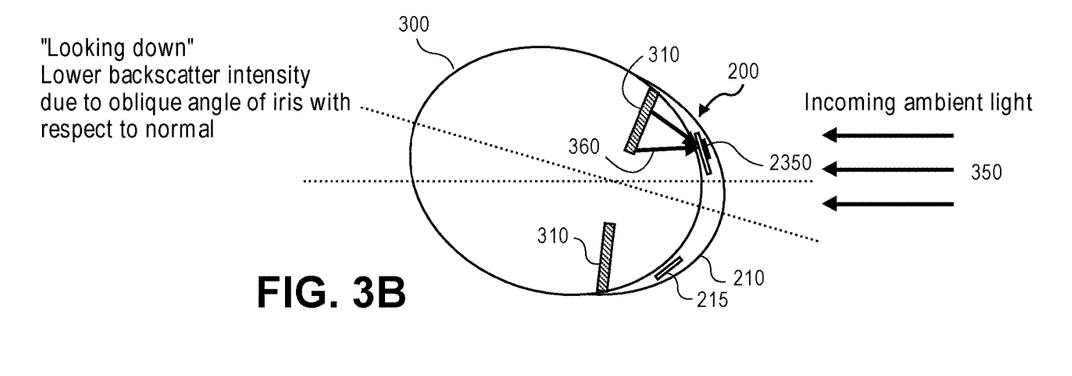

FIG. 3B shows cornea 300 of FIG. 3A looking down and ambient light 350 producing backscatter light 360 from iris 310. In this downward looking position, the intensity of backscatter light 360 is less than an intensity of backscatter light 360 when cornea 300 is looking straight forward. A portion of backscatter light 360 is detected by photosensor 2350 and converted to a current signal that is less than the baseline signal. Correspondingly (see FIG. 3B), if controller 225 determines, based upon a current signal from one or more photosensors, that the cornea is looking down and inward towards the nose, then it can be assumed the user is focusing on the near-field (e.g., reading). In this scenario, the amount of accommodation applied by accommodation actuator 230 should correspond to a near-field focal distance associated with the activity of reading.

Detecting backscattered or reflected light from an iris of a wearer provides orientation agnostic signals to track eye position, particularly positions of looking downward and straight ahead that may be used to modify accommodation of eye-mountable device 200. An iris of an eye acts as an averaging filter for incident light on the eye. Thus, backscattered light from the iris measured at a single physical location can be used to indicate a position of the entire eye. Because the signals representative of backscattered light are orientation agnostic, the eye position signals are independent of any rotation of eye-mountable device 200 on a wearer of the device. Further, an eye position may be determined using a single photosensor (e.g., on photodiode) to detect backscatter light from an iris. In another embodiment, more than one photosensor is used to improve light detection measurement under varying light conditions. For example, one or more photosensors may be configured for a frequency to capture reflected or backscattered light from an iris when the ambient light is an indoor light while one or more other photosensors on the same eye-mountable device may be configured for a frequency to capture reflected or backscattered light from an iris when the ambient light is sunlight. In another embodiment, one or more photosensors may be oriented with a light-detecting surface facing outward to detect ambient light intensity and provide this information to a controller of an eye-mountable device for the controller to adjust a baseline signal relative to light intensity. Still further, the use of additional photosensors capable of measurement of electromagnetic radiation outside of the visible spectrum (390-700 nm) may be also be implemented independently and/or in combination with photosensors operating in the visible range. In particular, photosensors in the near infra-red (NIR) (750-1000 nm) are well suited for iris backscatter applications as the absorption spectrum of melanin is strongly absorbing in the visible but less so in the near infra-red. Similarly, ultraviolet-based sensors that make use of wavelengths below 390 nm may be useful in detecting backscatter outside the strongly absorbing region of the iris and may also be useful in detecting ambient sunlight conditions.

Accommodation actuator 230 is centrally positioned within enclosure material 210 to affect the optical power of eye-mountable device 200 in the user's center of vision. In various embodiments, accommodation actuator 230 operates by changing is index of refraction under the influence of controller 225. By changing its refractive index, the net optical power of the curved surfaces of eye-mountable device 200 is altered, thereby applying controllable accommodation. Accommodation actuator 230 may be implemented using a variety of different electro-active optical devices. For example, accommodation actuator 230 may be implemented using a layer of liquid crystal (e.g., a liquid crystal cell) disposed in the center of enclosure material 210. In other embodiments, accommodation actuator 230 may be implemented using other types of electro-active optical materials such as electro-optic materials that vary refractive index in the presence of an applied electric field. Accommodation actuator 230 may be a distinct device embedded within enclosure material 210 (e.g., liquid crystal cell), or a bulk material having a controllable refractive index. In yet another embodiment, accommodation actuator 230 may be implemented using a deformable lens structure that changes shape under the influence of an electrical signal. Accordingly, the optical power of eye-mountable device 200 is controlled by controller 225 with the application of electric signals via one or more electrodes extending from controller 225 to accommodation actuator 230.

Accommodation actuator 230 may be implemented using a variety of different liquid crystal structures including nematic liquid crystal, nematic twisted liquid crystal, cholesteric liquid crystal, or blue phase liquid crystal. Since a low switching voltage is desirable for low power chip design, nematic liquid crystals with switching voltages less than 5 V are suitable. With the application of a 5V control signal, refractive index switching ranging from approximately 1.74 in an off-mode to 1.52 in an on-mode is achievable. A refractive index shift of 0.2 should be sufficient to provide near-field accommodation for reading.

Returning to FIG. 2A, loop antenna 240 is a layer of conductive material patterned along the flat surface of the substrate to form a flat conductive ring. In some examples, to allow additional flexibility along the curvature of the enclosure material, loop antenna 240 can include multiple substantially concentric sections electrically joined together. Each section can then flex independently along the concave/convex curvature of eye-mountable device 200. In some examples, loop antenna 240 can be formed without making a complete loop. For instances, antenna 240 can have a cutout to allow room for controller 225 and power supply 220, as illustrated in FIG. 2A. However, loop antenna 240 can also be arranged as a continuous strip of conductive material that wraps entirely around the flat surface of substrate 215 one or more times. For example, a strip of conductive material with multiple windings can be patterned on the backside of substrate 215 opposite controller 225, power supply 220, and photosensor system 235. Interconnects between the ends of such a wound antenna (e.g., the antenna leads) can then be passed through substrate 215 to controller 225.

Since eye-mountable device 100 may be worn by different users having a variety of different eye sizes and eyelid shapes, a configuration process may be useful to train the system for a particular user or wearer. Accordingly, a gaze detection calibration may be executed upon an initial use (or even on a periodic basis) to acquire baseline readings for different gaze directions and focal distances.

Figure 4:
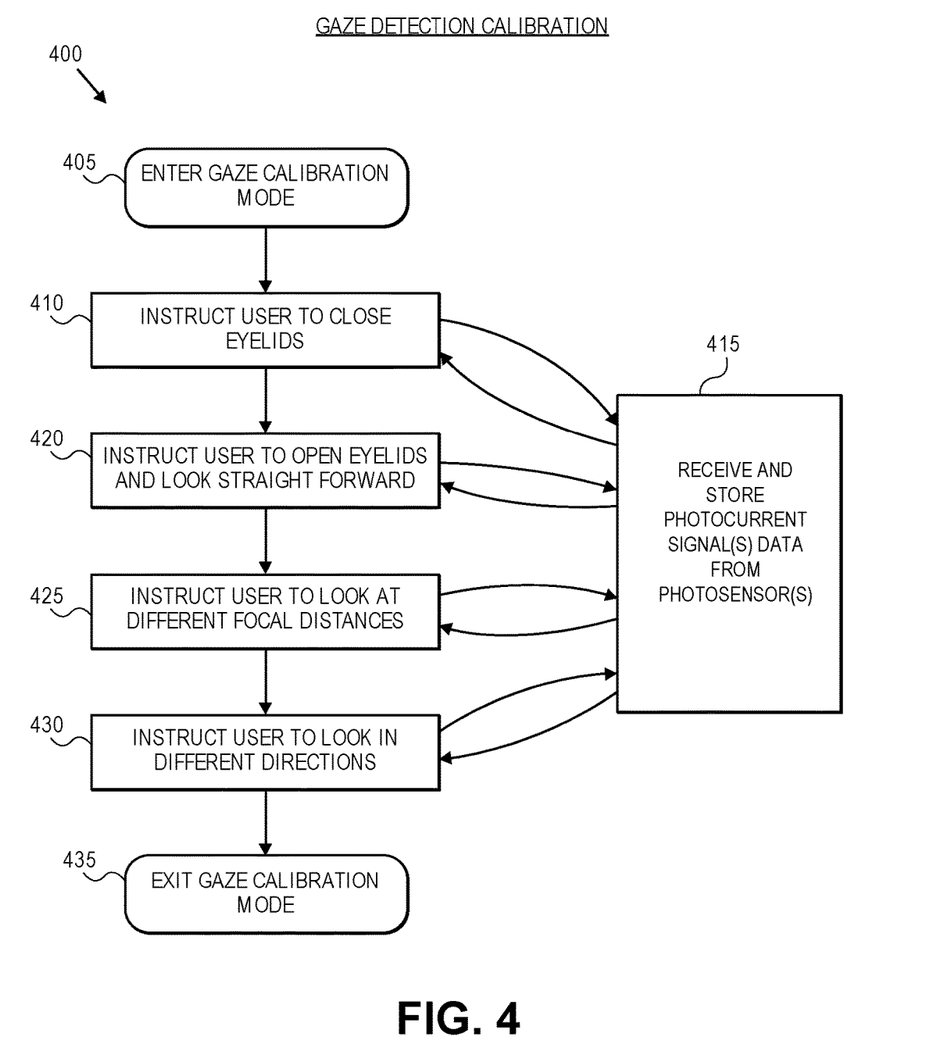
FIG. 4 is a flow chart illustrating a process for calibration of an eye-mountable device, in accordance with an embodiment of the disclosure.

FIG. 4 is a flow chart illustrating a process 400 for calibration of an eye position or gaze detection mechanism of eye-mountable device 100 described with reference to FIG. 1, in accordance with an embodiment of the disclosure. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

In a process block 405, controller 125 enters a gaze calibration mode. In one embodiment, gaze calibration mode is activated wirelessly via reader 105. In other embodiments, gaze calibration mode may be activated via a particular sequence of eye blinks sensed using photosensor system 135. In yet other embodiments, an optical sensor may be included on substrate 115 to pick up user commands via blink sequences.

Once gaze calibration mode is engaged, the user may be prompted to position their eyes in a series of gaze directions/ focal distances while baseline photocurrent measurements are acquired. These photocurrent measurements may be used to both associate baseline photocurrent values with particular gaze directions and/or focal distances, but also to determine and/or confirm the rotational position of eye-mountable device 100. For rotational-stable contact lenses (e.g., weighted lenses or toric lenses), positional measurements may not be necessary. For non-rotationally stable contact lenses, a position calibration may be periodically re-executed or continuously monitored.

Process blocks 410 through 430 describe an example calibration sequence; however, it should be appreciated that in various other embodiments the user may be prompted to look in fewer gaze directions/focal distances, more gaze directions/focal distances, and/or alternative gaze directions/focal distances. In a process block 410, the user is prompted to close their eyelids. In one embodiment, the user may be prompted on a display screen or from an audible speaker of reader 105. In other embodiments, eye-mountable device 100 may include a pixel array capable of providing visual prompts. Once the user closes their eyelids, controller 125 measures the photocurrent value(s) of photosensor system 135 and stores the photocurrent values as baseline reference values associated with closed eyelids (process block 415).

In a process block 420, the user is prompted to open their eyelids and look straight forward at an object that is greater than several meters away (i.e., far field object). Again, in process block 415, controller 125 reads a current signal from photosensor system 135 (representing a measurement of amount of backscatter light from an iris of the eye) and stores the current amount as a baseline current value associated with a far-field gaze direction.

In a process block 425, the user is prompted to look at one or more different focal distance by staring at objects at a specified distance from the user. Between each prompting, process 400 returns to process block 415, where controller 125 receives current signal data from photosensor system 135 and stores the current data as reference data associated with the prompted focal distance. For example, the user may be asked to read a book and the current signal received by controller 125 at that time is then associated with the near-field activity of reading.

In a process block 430, the user is prompted to look in one or more different directions such as up, down, left, or right. Between each prompting, process 400 returns to process block 415, where controller 125 receives current signals from photosensor system 135 and stores the current signal data as data associated with the prompted gaze direction. One or more of the measurements associated with process block 430 may also be executed independent of the other process blocks of process 400 to periodically determine the rotational position of eye-mountable device 100 on the cornea.

After all calibration measurements have been acquired, controller 125 exits the gaze calibration mode (process block 435).

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An eye-mountable device comprising:
    an enclosure formed to be removably mounted on a corneal surface of an eye and to be compatible with a motion of an eyelid;
    a photosensor embedded in the enclosure, the photosensor comprising a light detecting surface oriented to detect light reflected from an iris of the eye; and
    an accommodation actuator embedded in the enclosure and coupled to the photosensor, wherein an optical power of the accommodation actuator is modified in response to an amount of light detected by the photosensor.

2. The eye-mountable device of claim 1, wherein the photosensor is a photodiode operable to convert detected light into a current signal.

3. The eye-mountable device of claim 1, further comprising a controller embedded in the lens enclosure and electrically connected to the photosensor and the accommodation actuator, wherein the controller comprises logic that when executed by the controller causes the controller to modify the optical power of the accommodation actuator in response to the light detected by the photosensor.

4. The eye-mountable device of claim 3, wherein a first amount of light detected by the photosensor is associated with a determination that a cornea of the eye is looking substantially forward and a second amount of light detected by the photosensor that is less than the first amount is associated with a determination that the cornea of the eye is looking downward.

5. The eye-mountable device of claim 4, wherein in response to a signal from the photosensor associated with the second amount of light, the controller is operable to modify the optical power of the accommodation actuator to improve a near-field focus.

6. The eye-mountable device of claim 4, wherein in response to a signal from the photosensor associated with the first amount of light, the controller is operable to modify the optical power of the accommodation actuator to improve a far-field focus.

7. The eye-mountable device of claim 1, wherein the photosensor is positioned in the lens enclosure so that when the eye-mountable device is mounted on a corneal surface of the eye, the photo sensor is in an area corresponding to the iris of the eye.

8. An eye-mountable device comprising:
an enclosure;
a substrate embedded in the enclosure and arranged in an outer perimeter of the enclosure so that at least a portion of the enclosure is over an iris of an eye, wherein the substrate is annular-shaped;
a photosensor disposed on the substrate, the photosensor comprising a light detecting surface oriented to detect light reflected from the iris of the eye; and
an accommodation actuator disposed in an inner diameter of the substrate and coupled to the photosensor, wherein an optical power of the accommodation actuator is modified in response to an amount of light detected by the photosensor.

9. The eye-mountable device of claim 8, wherein the photosensor is a photodiode operable to convert detected light into a current signal.

10. The eye-mountable device of claim 8, further comprising a controller disposed on the substrate and electrically connected to the photosensor and the accommodation actuator, wherein the controller comprises logic that when executed by the controller causes the controller to modify the optical power of the accommodation actuator in response to the amount of light detected by the photosensor.

11. The eye-mountable device of claim 10, wherein a first amount of light detected by the photosensor is associated with a determination that a cornea of the eye is looking substantially forward and a second amount of light detected by the photosensor that is less than the first amount is associated with a determination that the cornea of the eye is looking downward.

12. The eye-mountable device of claim 11, wherein in response to a signal from the photosensor associated with the second amount of light, the controller is operable to modify the optical power of the accommodation actuator to improve a near-field focus.

13. The eye-mountable device of claim 11, wherein in response to a signal from the photosensor associated with the first amount of light, the controller is operable to modify the optical power of the accommodation actuator to improve a far-field focus.

14. A method comprising:
monitoring a signal from a photosensor embedded in an enclosure, the signal representative of light reflected from an iris of an eye on which the enclosure is mounted;
detecting a change in a gazing direction of the eye based on the signal; and
modifying an optical power of an accommodation actuator embedded in the enclosure in response to the detected change in gazing direction.

15. The method of claim 14, wherein modifying an optical power of the accommodation actuator comprises providing a voltage to an electro-active material to change an index of refraction of the electro-active optical material.

16. The method of claim 14, wherein a first signal from the photosensor is associated with a determination that a cornea of the eye is looking substantially forward and a second signal from the photosensor that is less than the first amount is associated with a determination that the cornea of the eye is looking downward.

17. The method of claim 16, wherein, in response to a signal from the photosensor associated with the second amount of light, modifying the optical power of the accommodation actuator comprises modifying the optical power to improve a near-field focus.

18. The method of claim 16, wherein, in response to a signal from the photosensor associated with the second amount of light, modifying the optical power of the accommodation actuator comprises modifying the optical power to improve a far-field focus.

19. The method of claim 14, wherein the photosensor is a photodiode.

* * * * *